United States Patent [19]

Cevasco

[11] Patent Number: 5,362,911
[45] Date of Patent: Nov. 8, 1994

[54] PROCESS FOR THE PREPARATION OF O-AMINOPHENYL CYCLO-PROPYL KETONE

[75] Inventor: Albert A. Cevasco, Belle Mead, N.J.

[73] Assignee: American Cyanamid Company, Wayne, N.J.

[21] Appl. No.: 175,823

[22] Filed: Dec. 30, 1993

[51] Int. Cl.$^5$ .................................................. C07C 209/74
[52] U.S. Cl. ................................................... 564/305
[58] Field of Search ........................................ 564/305

[56] References Cited

U.S. PATENT DOCUMENTS

| | | | |
|---|---|---|---|
| 4,160,784 | 7/1979 | Sugasawa et al. | 260/570 AB |
| 4,622,065 | 11/1986 | Van Gemert | 71/93 |
| 4,769,483 | 9/1988 | Lombardi et al. | 560/19 |
| 5,009,699 | 4/1991 | Brady et al. | 71/92 |
| 5,107,023 | 4/1991 | Brady et al. | 564/305 |

OTHER PUBLICATIONS

George W. Cannon, et al., Organic Syntheses, 1963, Collective vol. 4, pp. 597–600.

*Primary Examiner*—Peter O'Sullivan
*Attorney, Agent, or Firm*—John W. Hogan, Jr.

[57] ABSTRACT

There is provided an effective method for the preparation of o-aminophenyl cyclopropyl ketone via the dehydrohalogenation of 1-(o-aminophenyl)-4-halo-1-butanone in the presence of a base and a phase transfer catalyst.

11 Claims, No Drawings

PROCESS FOR THE PREPARATION OF O-AMINOPHENYL CYCLO-PROPYL KETONE

BACKGROUND OF INVENTION

The compound o-aminophenyl cyclopropyl ketone is a useful intermediate in the manufacture of crop-selective sulfamoyl urea herbicidal agents. It is particularly useful in the manufacture of 1-(o-cyclopropylcarbonyl)-phenylsulfamoyl urea derivatives which are highly potent, yet environmentally benign, cereal crop tolerant herbicides. Methods known to prepare o-aminophenyl cyclopropyl ketone such as those described in U.S. Pat. Nos. 4,160,784 and 5,009,699 use cyclopropylnitrile as starting material. However, cyclopropylnitrile is not commercially nor readily obtainable, whereas 4-chlorobutyronitrile is obtainable commercially. However, there is no effective method available to prepare o-aminophenyl cyclopropyl ketone from its 4-halo acyclic precursor, 1-(o-aminophenyl)-4-halo-1-butanone.

Therefore, it is an object of this invention to provide an effective process for the preparation of o-aminophenyl cyclopropyl ketone via the dehydrohalogenation of 1-(o-aminophenyl)-4-halo-1-butanone.

It is another object of this invention to provide a source of a useful intermediate in the manufacture of herbicidal sulfamoyl urea derivatives.

SUMMARY OF INVENTION

The present invention provides a process for the preparation of o-aminophenyl cyclopropyl ketone which comprises reacting a compound of formula I wherein X is chlorine or bromine with at least one molar equivalent of an aqueous base in the presence of a phase transfer catalyst and optionally in the presence of an organic solvent.

The use of the product o-aminophenyl cyclopropyl ketone as a key intermediate in the manufacture of a potent, crop-selective, sulfamoyl urea herbicidal agent is described in U.S. Pat. No. 5,107,023.

The preparation of compounds of formula I is described in U.S. Pat. No. 4,160,784 and co-pending patent application Ser. No. 08/159,984 (Attorney Docket No. 32,340) filed on Nov. 30, 1993.

DETAILED DESCRIPTION OF THE INVENTION

Sulfamoyl urea derivatives are useful as herbicidal agents and in particular, 1-{o-(cyclcpropylcarbonyl)-phenyl]sulfamoyl}-3- (4,6-dimethoxy-2-pyrimidinyl-)urea is useful as a potent, environmentally benign herbicide with cereal crop selectivity. A key intermediate in the manufacture of this herbicide is cyclopropyl o-aminophenyl cyclopropyl ketone. It has now been found that this important intermediate compound may be effectively prepared with minimal sideproduct formation by the dehydrohalogenation of 1-(o-aminophenyl)-4-halo-1-butanone using at least one molar equivalent, preferably 1.1 - 3.0 molar equivalents, of an aqueous base in the presence of a phase transfer catalyst and optionally in the presence of an organic solvent.

Although the dehydrohalogenation of a γhaloalkyl ketone using aqueous base is known to form the corresponding cycloalkyl ketone, for example, as described in Organic Synthesis, Coll. Vol. 4, pp. 597–600 (1963), when these procedures are applied to 4-halobutanone compounds of formula I wherein X is chlorine or bromine, the reaction proceeds slowly and the major product is mainly the 4-hydroxy analogue of formula II.

Surprisingly, it has been found that when a phase transfer catalyst (PTC) is present in the reaction mixture, the reaction rate is effectively increased and the major product is the desired cyclopropyl ketone of formula III. The reaction scheme is shown in flow diagram I.

Flow Diagram I

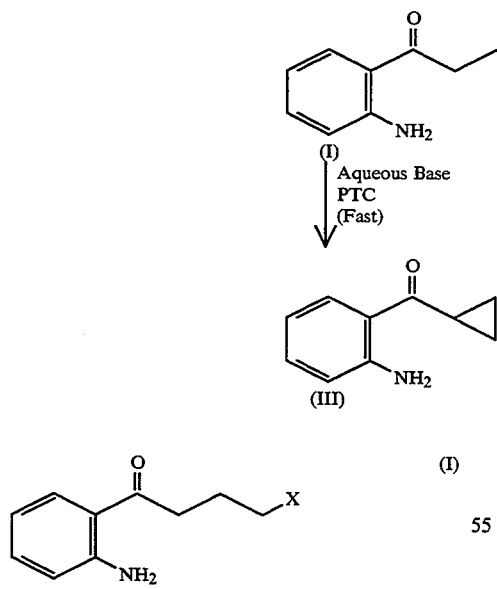

Phase transfer catalysts suitable for use in the inventive process are those well known in the art such as, quaternary ammonium salts, for example trialkyl ammonium salts or tetralkylammonium salts, preferably tri-or tetrabutylammonium halides. An effective amount of the catalyst may range from about 0.001–0.50 molar equivalents.

Aqueous bases suitable for the preparation of o-aminophenyl cyclopropyl ketone by the present process include sodium and potassium hydroxide, carbonate or bicarbonate or mixtures thereof at concentrations in aqueous solution of about 15% to 50% by weight in amounts sufficient to provide at least one molar equivalent, preferably about 1.1 to 3.0 molar equivalents, and more preferably about 1.5 to 2.5 molar equivalents.

The organic solvent may be any inert water immiscible solvent or mixtures of solvents such as halogenated hydrocarbons, alkyl and aromatic ethers, aromatic hydrocarbons, halogenated aromatic hydrocarbons, and the like, preferably halogenated hydrocarbons such as methylene dichloride, ethylene dichloride, propylene dichloride and the like.

In accordance with the process of the invention, a 4-halobutanone compound of formula I, optionally dissolved in an organic solvent or mixture of solvents, is admixed with at least one molar equivalent of an aqueous base, preferably about 1.1–3.0 molar equivalents, more preferably about 1.5–2.5 molar equivalents and a quaternary ammonium phase transfer catalyst, preferably methyl tributylammonium chloride, in an amount of about 0.001–0.50 molar equivalents, preferably about 0.025–0.50 molar equivalents.

For a more clear understanding of the invention, specific examples thereof are set forth below. These examples are merely illustrative and are not to be understood as limiting the scope and underlying principles of the invention in any way.

The terms HPLC and GC designate high performance liquid chromatography and gas chromatography, respectively.

EXAMPLE 1

Preparation of o-aminophenyl cyclopropyl ketone via the Dehydrohalogenation of 1-(o-aminophenyl)-4-chloro-1-butanone in the Presence of a Phase Transfer Catalyst

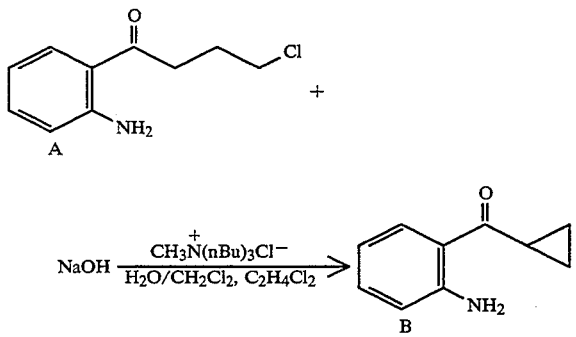

A solution of 1-(o-aminophenyl)-4-chloro-1-butanone (32.6 g, 0.165 mole) in ethylenedichloride is treated with 147.3 g of 20% aqueous NaOH (0,736 mole NaOH) and 2.31 g of 75% aqueous methyl tributylammonium chloride(0.0074 mole), and stirred at 50°–53°0 C. for about 4 hours. (Samples are removed at intervals and analyzed by HPLC.) The reaction is cooled to room temperature and the phases are separated. The organic phase is washed with water and concentrated in vacuo to give the title product, 29.84 g, 70.6% pure, 79.2% yield by HPLC and GC analyses.

Reaction progress is shown in Table I.

TABLE I

| Sample | Time h | % A | % B |
|---|---|---|---|
| 1 | 0.0 | 100.0 | 0.0 |
| 2 | 0.5 | 28.4 | 66.9 |
| 3 | 1.0 | 12.2 | 80.6 |
| 4 | 3.0 | 0.5 | 94.6 |
| 5 | 4.0 | 0.0 | 96.3 |

EXAMPLE 2

Evaluation of the Effect of a Phase Transfer Catalyst on the Dehydrohalogenation of 1-(o-aminophenyl)-4-chloro-1-butanone

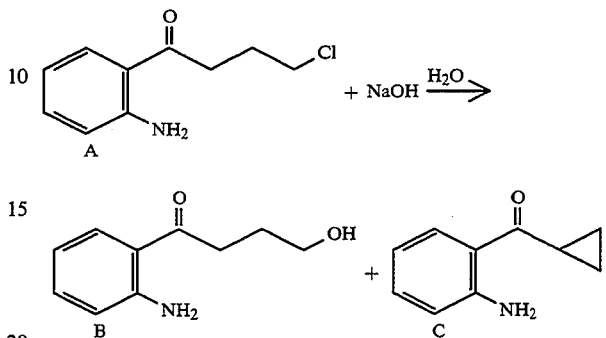

GENERAL PROCEDURE

A mixture of 1-(o-aminophenyl)-4-chloro-1-butanone (35.6 g, 0.18 mole) in a solvent mixture of ethylene dichloride and methylene dichloride and 146 g of 20% aqueous NaOH (0.73 mole) is stirred at 50°–85° C. for 9 hours. After the 9 hour period, methyl tributylammonium chloride (1.74 g, 0.0074 mole) is added and stirring is continued for an additional 0.5 hour. Aliquots of the reaction mixture are removed at 0.5– 1 hour(h) time intervals and are assayed for the presence of starting material (A), 1-(o-aminophenyl)-4-hydroxy-1-butanone (B) and o-aminophenyl cyclopropyl ketone (C). The results are recorded and shown in Table II below. The assays are performed using HPLC. analysis.

TABLE II

| Sample | Time h | Temp. °C. | % A | % B | % C |
|---|---|---|---|---|---|
| 1 | 0 | 50 | 92.0 | 1.0 | 0.0 |
| 2 | 0.5 | 50 | 85.6 | 0.9 | 0.5 |
| 3 | 1.0 | 50 | 89.0 | 1.5 | 1.8 |
| 4 | 2.0 | 50 | 89.4 | 2.2 | 0.8 |
| 5 | 3.0 | 50 | 91.2 | 3.8 | 1.1 |
| 6 | 4.0 | 50 | 83.0 | 3.8 | 1.0 |
| 7 | 5.0 | 67 | 86.4 | 6.9 | 1.5 |
| 8 | 6.0 | 67 | 83.0 | 7.8 | 1.7 |
| 9 | 7.0 | 67 | 78.0 | 14.1 | 3.2 |
| 10 | 8.0 | 76 | 73.0 | 19.2 | 3.5 |
| 11 | 9.0 | 85 | 51.8 | 33.5 | 7.1 |
| 12 | 9.5 | 85 | 0.0 | 34.3 | 56.0 |

As can be seen from Table II above, in the absence of a phase transfer catalyst (samples 1–11) the starting 4-chlorobutanone (A) is preferentially and slowly converted to the unwanted 4-hydroxybutanone byproduct (B). However, 0.5 hour after the addition of the phase transfer catalyst (sample 12), the starting material is completely converted to, preferentially, the desired cyclopropyl ketone product (C). Hence, the reaction rate to the desired product (C) is about 250 times greater in the presence of a phase transfer catalyst than in the absence of a phase transfer catalyst.

I claim:

1. A process for the preparation of o-aminophenyl cyclopropyl ketone which comprises reacting a compound of formula I

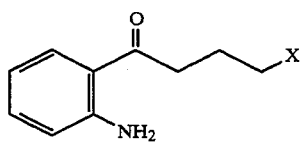

wherein X is chlorine or bromine with at least one molar equivalent of an aqueous base in the presence of a phase transfer catalyst and optionally in the presence of an organic solvent.

2. The process according to claim 1 wherein X is chlorine.

3. The process according to claim 1 wherein the organic solvent is present and is ethylene dichloride, methylenedichloride, propylenedichloride or mixtures thereof.

4. The process according to claim 1 wherein the aqueous base is an alkali metal base.

5. The process according to claim 4 wherein the alkali metal base is NaOH or KOH.

6. The process according to claim 5 wherein the base is NaOH.

7. The process according to claim 1 wherein the aqueous base is present in an amount of about 1.5 to 2.5 molar equivalents.

8. The process according to claim 1 wherein the phase transfer catalyst is a trialkylammonium halide or a tetraalkylammonium halide.

9. The process according to claim 8 wherein the phase transfer catalyst is a tetraalkylammonium halide.

10. The process according to claim 9 wherein the phase transfer catalyst is methyl tributylammonium chloride.

11. The process according to claim wherein the aqueous base is NaOH.

* * * * *